US009116143B2

(12) United States Patent
Jegou et al.

(10) Patent No.: US 9,116,143 B2
(45) Date of Patent: Aug. 25, 2015

(54) SYSTEM FOR MEASURING OR MONITORING THE QUALITY OF A LIQUID MEDIUM WITH LOW ENERGY CONSUMPTION

(75) Inventors: Paul Jegou, Brest (FR); David Le Piver, Brest (FR); Christian Podeur, Brest (FR); Patrice Woerther, Plouzane (FR)

(73) Assignee: Institut Francais De Recherche Pour L'Exploitation De La Mer—IFREMER, Issy-les-Moulineaux Cedex (FR)

( * ) Notice: Subject to any disclaimer, the term of this patent is extended or adjusted under 35 U.S.C. 154(b) by 337 days.

(21) Appl. No.: 13/697,088

(22) PCT Filed: May 5, 2011

(86) PCT No.: PCT/EP2011/057179
§ 371 (c)(1),
(2), (4) Date: Nov. 9, 2012

(87) PCT Pub. No.: WO2011/141343
PCT Pub. Date: Nov. 17, 2011

(65) Prior Publication Data
US 2013/0055796 A1    Mar. 7, 2013

(30) Foreign Application Priority Data

May 10, 2010    (FR) .................................... 10 53622

(51) Int. Cl.
*G01N 1/00*     (2006.01)
*G01N 33/18*    (2006.01)
*G01N 1/20*     (2006.01)
*G01N 1/16*     (2006.01)

(52) U.S. Cl.
CPC .......... *G01N 33/1886* (2013.01); *G01N 1/2035* (2013.01); *G01N 1/16* (2013.01)

(58) Field of Classification Search
CPC .............. G01N 1/12; G01N 1/24; G01N 1/08
USPC .................. 73/863.31, 64.56, 61.59, 860, 170
See application file for complete search history.

(56) References Cited

U.S. PATENT DOCUMENTS

| 4,470,316 A * | 9/1984 | Jiskoot ........................ 73/863.84 |
| 5,633,460 A | 5/1997 | Manmaru et al. |
| 6,925,895 B2 * | 8/2005 | Barker ........................ 73/864.34 |
| 8,181,504 B2 * | 5/2012 | Tewarson ..................... 73/23.41 |

FOREIGN PATENT DOCUMENTS

| DE | 3024473 | * | 1/1981 | ............. G01N 33/18 |
| FR | 2264278 | * | 10/1975 | ............... G01N 1/10 |
| FR | 2461254 A1 | | 1/1981 | |
| FR | 2741446 | * | 5/1997 | ............. G01N 33/18 |
| FR | 2741446 A1 | | 5/1997 | |

* cited by examiner

*Primary Examiner* — Hezron E Williams
*Assistant Examiner* — Truong Phan
(74) *Attorney, Agent, or Firm* — Bachman & LaPointe, P.C.

(57) ABSTRACT

A system for measuring or monitoring the quality of a liquid medium, has first and second sample-takeoff points in the liquid medium and a hydraulic circuit in which the samples taken off from said first and second sample-takeoff points circulate. The hydraulic circuit is mounted between the two sample-takeoff points and comprises two centrifugal impeller pumps, a measuring chamber situated between the two pumps, and a purge device mounted at a high point on the hydraulic circuit between one of the pumps and the measuring chamber. The whole of the hydraulic circuit is preferably totally immersed in the liquid medium.

10 Claims, 3 Drawing Sheets

SYSTEM FOR MEASURING OR MONITORING THE QUALITY OF A LIQUID MEDIUM WITH LOW ENERGY CONSUMPTION

BACKGROUND

The present invention concerns, in general terms, the monitoring of the quality of a liquid medium and in particular more or less salty water in coastal areas or estuaries.

More precisely, the invention concerns a system for measuring or monitoring the quality of a liquid medium comprising first and second points for taking off a sample from the liquid medium and a hydraulic circuit in which the samples taken from the first and second sample-takeoff points circulate. The hydraulic circuit comprises in particular a measuring chamber provided with at least one measuring sensor able to measure a quantity characteristic of the liquid medium, such as a physicochemical or biological parameter of the liquid medium, said measuring chamber having a first opening in fluid communication with the first sample-takeoff point and a second opening, and a first suction pump having a suction inlet connected to the second opening of the measuring chamber and a discharge opening in fluid communication with the liquid medium, the first suction pump being able, in operating configuration, to circulate in the hydraulic circuit a sample taken from the first sample-takeoff point.

A measuring or monitoring system of this type is for example described in the patent application FR 2 741 446.

To function correctly, this system is supplemented by a de-aerator placed above the first pump in order to trap the gases present in the circuit when the system is started up as well as the gases issuing from the natural degassing of the sampled liquid. It also comprises a priming pump connected to the de-aerator in order to prime the hydraulic circuit at the start of operation and a sample-takeoff system for selectively connecting the sample-takeoff points to the inlet and outlet of the hydraulic circuit.

Although giving complete satisfaction with regard to its performance, this measuring system has a few characteristics that could be improved, such as relatively high structural complexity and energy consumption.

SUMMARY OF THE INVENTION

In this context, the aim of the present invention is to propose a system for measuring or monitoring a liquid medium having reduced energy consumption as well as small size, and offering great ease of maintenance.

To this end, the measuring system of the invention, which is moreover in accordance with the generic definition given by the above preamble, is essentially characterised in that the hydraulic circuit also comprises a second suction pump having a suction inlet connected to the first opening of the measuring chamber and a discharge outlet in fluid communication with the liquid medium, said second suction pump being able, in the operating configuration, to circulate in the hydraulic circuit a sample taken from the second sample-takeoff point;

at least one conduit for connecting the first opening of the measuring chamber to the suction inlet of the second suction pump or connecting the second opening of the measuring chamber to the suction inlet of the first suction pump, said conduit being provided with a purge device placed at a high point of the hydraulic circuit in order to discharge the gases present in the hydraulic circuit, and in that the discharge outlet of the first suction pump is connected to the second sample-takeoff point and the discharge outlet of the second suction pump is connected to the first sample-takeoff point, said first and second suction pumps being, at rest, able to allow the passage of liquid from their discharge outlet to their suction inlet.

Thus, according to the invention, the monitoring system comprises two suction pumps placed on either side of the measuring chamber. By virtue of this arrangement, the liquid samples taken at the first and second takeoff points circulate in opposite directions in the measuring chamber and all the elements of the hydraulic circuit in which the liquid samples circulate are placed in line (no element mounted in a bypass). As a result the pressure drop suffered by the liquid in movement in the hydraulic circuit is low, which makes it possible to use suction pumps having reduced nominal power. This in-line arrangement also contributes to reducing deposition in the hydraulic circuit of solid elements such as sediments.

In order to facilitate maintenance of the system and to protect against biosoiling, the hydraulic circuit also advantageously comprises a means of generating or injecting biocide product placed between said first and second takeoff points. The biocide product to be used is determined according to the liquid medium to be treated. It is for example chlorine when the system is intended to be used in salt water. The in-line arrangement of all the elements of the circuit then makes it possible, through the simple circulation of the liquid in the circuit, to protect all these elements and to place the generation or injection point anywhere on the line. However, for reasons of alternation of the direction of circulation and proximity of the sensors to be protected, this injection or generation point is advantageously mounted on the measuring chamber.

Advantageously, the first and second suction pumps are suited to immersion and are, in the operating configuration, immersed in the liquid medium.

According to a preferred embodiment, the purge device is also suitable for immersion and is immersed in the liquid medium. In this embodiment, the purge device being positioned at a high point in the hydraulic circuit, the hydraulic circuit is entirely immersed in the liquid medium.

According to a particular embodiment, the purge device advantageously comprises a valve system for discharging the gases present in the hydraulic circuit.

According to a particular embodiment, the purge device comprises:

a substantially vertical tubular body mounted by its bottom open end on a top opening of the conduit between the measuring chamber and the first or second suction pump, and a cylindrical valve able to slide in the internal passage in the tubular body and cooperate with a lower portion of the tubular body, forming a seat, to close off the bottom open end of said tubular body.

According to a particular embodiment, the internal wall of the lower portion of the tubular body comprises a frustoconical portion forming the seat of the valve. In this embodiment, the valve advantageously comprises a bottom portion the external wall of which comprises a frustoconical portion cooperating with the frustoconical portion of the internal wall of the tubular body in order to close off the bottom open end of the tubular body.

The tubular body and the valve of the automatic purge device are preferably made from anti-biosoiling copper alloy.

BRIEF DESCRIPTION OF THE DRAWINGS

Other features and advantages of the invention will emerge more clearly in the following detailed explanatory description, referring below to the accompanying drawings, which show.

DETAILED DESCRIPTION OF THE PREFERRED EMBODIMENT(S)

As indicated previously, the invention concerns a system for measuring or monitoring a liquid medium, in particular intended to detect any pollution in water, salty or not, to enable ecosystems to be modelled, or to make it possible to control certain operations relating to aquaculture, such as the irrigation of oyster maturation pools for example.

Figure 1:
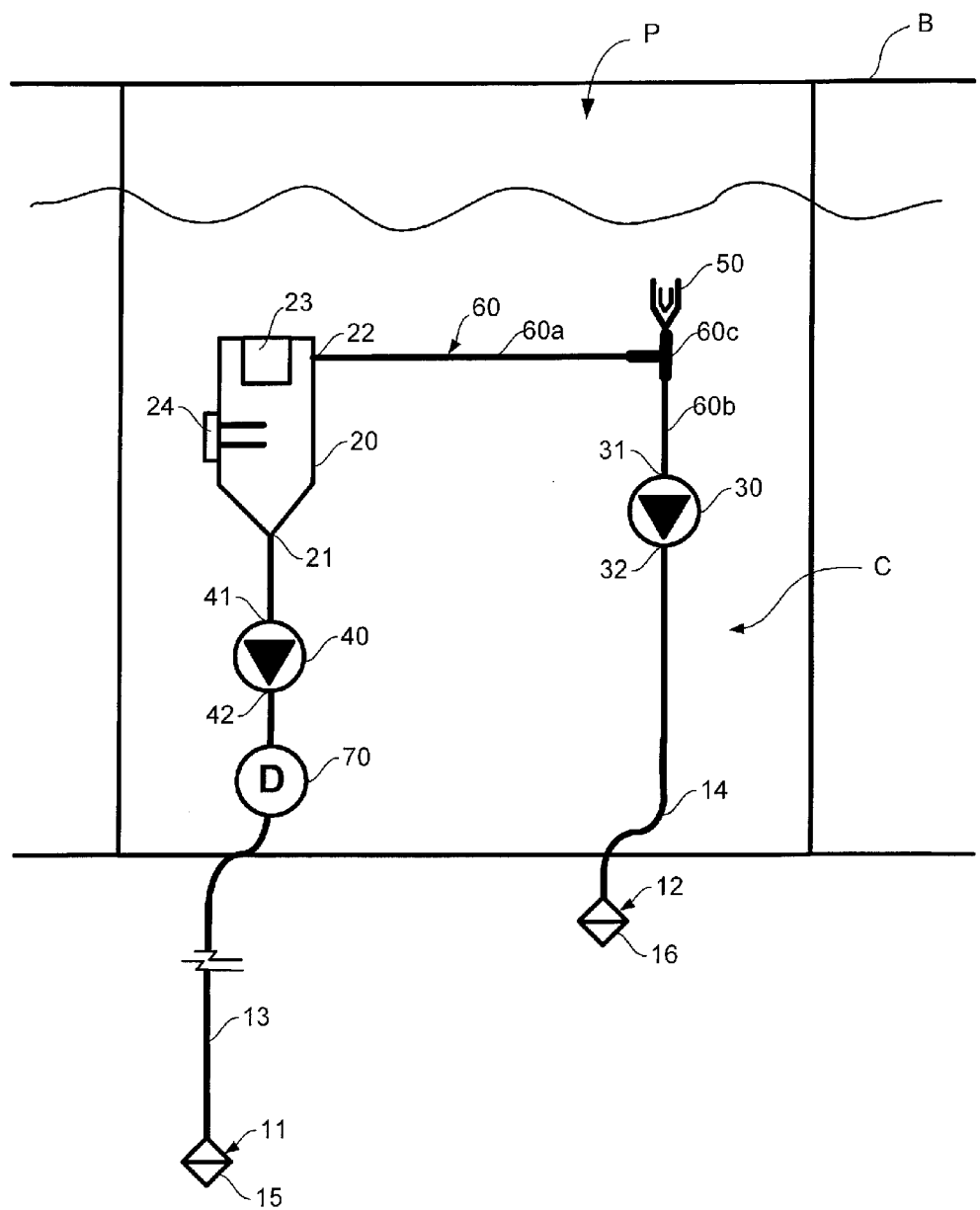
FIG. 1, the outline diagram of a measuring and monitoring system according to the invention.
Figure 2:
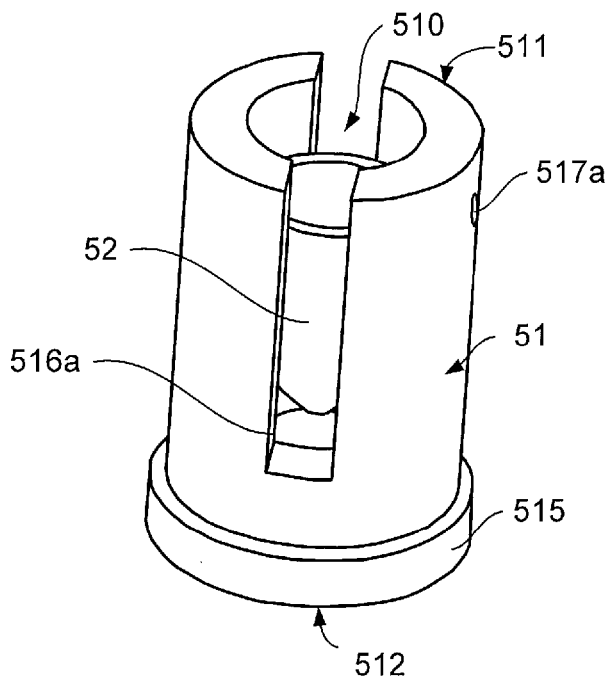
FIG. 2, an external perspective view of the purge device used in the measuring and monitoring system of the invention, said device comprising a tubular body and a valve able to slide in the internal passage in the tubular body.
Figure 3:
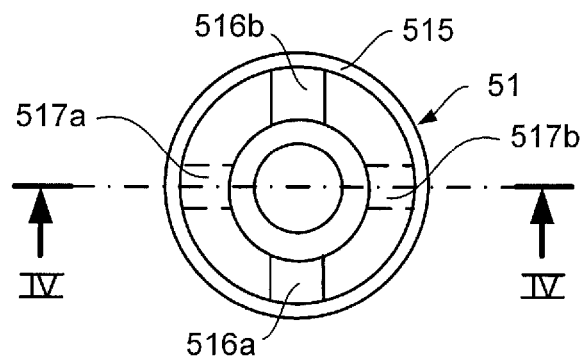
FIG. 3, a plan view of the tubular body of the purge device of FIG. 2.
Figure 4:
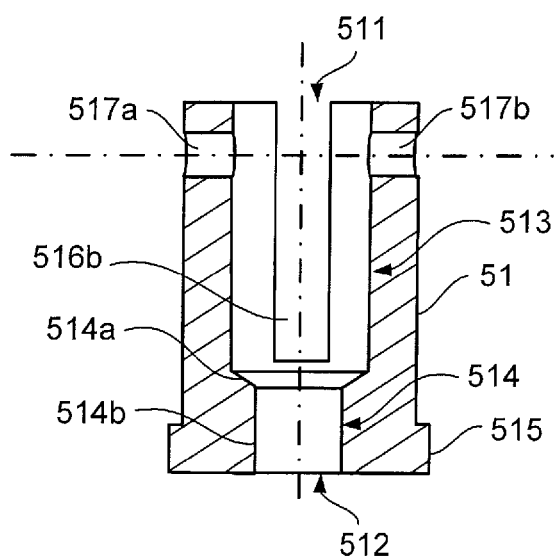
FIG. 4, a view in section of the tubular body, taken along the line IV-IV in FIG. 3.

With reference to FIG. 1, the measuring system comprises essentially a hydraulic circuit C mounted between two sample-takeoff points 11 and 12. This system is intended to be fully immersed in the liquid medium. It is installed in the well P of a buoy B or any other support.

The two sample-takeoff points 11 and 12, which correspond to the bottom end orifices of takeoff conduits 13 and 14, are preferably situated at different depths. These takeoff points are advantageously equipped with strainers, respectively 15 and 16, to filter the liquid admitted in the takeoff conduits 13 and 14.

The hydraulic circuit C comprises essentially a measuring chamber 20, two suction pumps 30 and 40 for taking off liquid samples at the sample-takeoff points 11 and 12, and a purge device 60 for discharging the gas present in the hydraulic circuit C.

The measuring chamber 20 is provided with one or more measuring sensors, for example in the form of a multi-parameter measuring probe 23, for measuring one or more characteristic quantities of the liquid medium to be characterised. These quantities are for example physicochemical or biological parameters of the liquid medium. These parameters are for example the temperature of the liquid, its electrical conductivity, its cloudiness, its pH, its dissolved oxygen concentration, and/or its chlorophyll concentration.

The measuring chamber 20, which is preferably placed in a substantially vertical configuration, has two openings, one 21 situated in its bottom part and the other 22 in its top part.

The pumps 30 and 40 are intended to bring into the measuring chamber 20 samples taken respectively at the sample-takeoff points 11 and 12.

The pumps 30 and 40 each have a suction inlet, respectively 31 and 41, and a discharge outlet, respectively 32 and 42.

The suction inlet 31 of the pump 30 is connected to the opening 22 of the measuring chamber via a conduit 60 and the discharge outlet 32 of the pump 30 is connected to the sample-takeoff point 12 via the takeoff conduit 14. The automatic purge device 50 is mounted on the conduit 60.

Likewise, the suction inlet 41 of the pump 40 is connected to the opening 21 of the measuring chamber 20 and the discharge outlet 42 is connected to the sample-takeoff point 11 via the takeoff conduit 13.

This arrangement of the pumps means that the samples taken off at the point 11 and the samples taken off at the point 12 circulate in opposite directions in the hydraulic circuit.

The pumps are advantageously immersed in the liquid medium and function in alternation, that is to say, when one of the pumps is in operation, the other is stopped and vice-versa. Between two operating phases, the two pumps are at rest, in particular in order to discharge the gases present in the hydraulic circuit.

According to an important feature of the invention, the pumps 30 and 40 are such that, at rest, they allow passage of liquid from their discharge outlet to their suction inlet. These are for example centrifugal impeller pumps.

Thus, with this method of operation and this type of pump, the liquid taken off at the sample-takeoff point 11 is, after passing through the hydraulic circuit, discharged at the sample-takeoff point 12 and vice-versa.

More precisely, when the pump 30 is in operation, it sucks liquid taken off at the sample-takeoff point 11. This liquid passes through the pump 40 at rest with a reduced pressure drop in order to reach the measuring chamber 20 and then passes through the pump 30 in order to be discharged in the liquid medium at the sample-takeoff point 12. Likewise, when the pump 40 is in operation, it sucks liquid taken off at the sample-takeoff point 12. This liquid passes through the pump 30 at rest with a reduced pressure drop in order to reach the measuring chamber 20 and then passes from the pump 40 in order to be discharged in the liquid medium at the sample-takeoff point 11.

The stirring produced by the pump in operation does not interfere with the measurements in the measuring chamber 20 since this pump is always the one that is placed downstream of the measuring chamber.

The measuring system of the invention advantageously comprises a means of generating biocidal product 24 placed between the two takeoff points 11 and 12. This biocidal product generating means is preferably mounted on the measuring chamber 20. When the system is intended to be used in salt water, this means 24 is for example a means of generating chlorine.

The hydraulic circuit being an in-line circuit, a flow meter may be interposed at any point on the circuit. In the example in FIG. 1, a flow meter 70 is mounted on the discharge outlet of the pump 40.

The hydraulic circuit also comprises a purge device 50 for discharging the gases present in the hydraulic circuit, in particular the gases present when said circuit is started up, the gases issuing from the natural degassing of the liquid in the circuit and the gases produced by the biocidal product generating device. This device is positioned at a high point on the hydraulic circuit, between the two pumps 30 and 40.

In the embodiment presented in FIG. 1, the purge device 50 is mounted on the conduit 60. In this example, the conduit 60 comprises a horizontal tubular portion 60a and a vertical tubular portion 60b connected together by a tubular portion 60c in the form of a T pivoted through 90° in the clockwise direction. More precisely, one of the ends of the horizontal portion 60a is connected to opening 22 of the measuring chamber and the other end is connected to the leg of the T. The top end of the vertical portion 60b is connected to one arm of the T, referred to as the bottom arm, and the bottom end is connected to the suction inlet 31 of the pump 30. Finally, the purge device 50 is mounted on the other arm of the T, referred to as the top arm.

According to a preferred embodiment illustrated by FIGS. 1 to 6, the automatic purge device 50 is a valve system.

This valve system comprises a roughly tubular body 51 having an internal passage 510, an open top end 511 and an open bottom end 512, and a roughly cylindrical valve 52 able to slide in the internal passage 510 in the tubular body.

More precisely, the internal passage in the tubular body comprises, from the top end 511 to the bottom end 512, a substantially cylindrical top part 513 and a bottom part 514 comprising a frustoconical portion 514a, which converges in the direction of the orifice situated at the bottom end 512 and defines a closure seat for the valve 52, extended by a substantially cylindrical end portion 514b.

The tubular body 51 is moreover provided, close to its bottom end 512, with an assembly collar 515 for assembly thereof, by screwing for example, to the top arm of the T-shaped portion 60c. It also comprises diametrically-opposed longitudinal slots 516a and 516b, provided in the cylindrical portion 513. These longitudinal slots may extend as far as the annular edge of the top end 511.

The tubular body 51 also comprises diametrically-opposed openings 517a and 517b, provided in the cylindrical portion 513 close to the annular edge of the top end 511. These openings are intended to receive a pin (not shown) intended to prevent the valve 52 from leaving the internal passage 510 in the tubular body.

Figure 5:
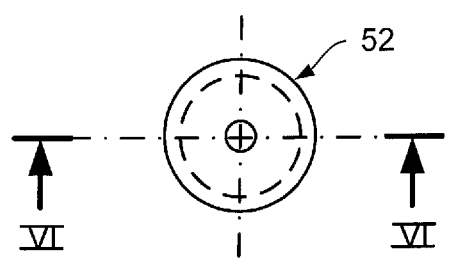
FIG. 5, a view from below of the valve of the purge device of FIG. 2.
Figure 6:
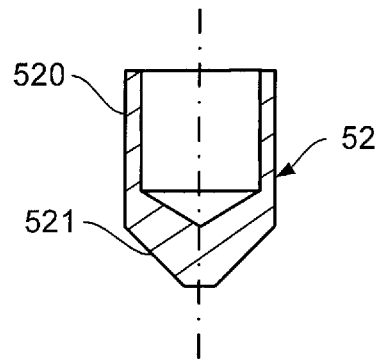
FIG. 6, a view in section of the valve taken along the line VI-VI in FIG. 5.

With reference to FIGS. 5 and 6, the valve 52 is formed from a roughly cylindrical top portion 520 extended by a bottom portion 521 of frustoconical shape.

In the absence of any gas in the hydraulic circuit and when the pumps 30 and 40 are at rest, the frustoconical portion 521 of the valve 52 comes into abutment by gravity on the frustoconical portion 514a and closes off the orifices in the bottom end 512 of the tubular body. The weight of the valve 52 is defined so that, when gas is present in the conduit 60, the valve 52 lifts and this gas escapes outside the hydraulic circuit by passing through the portion 514 and the longitudinal slots 517a and 517b in the tubular body. The weight of the valve is for example defined so as to open under the effect of a gas bubble 1 cm in height under the valve. In the example in FIGS. 2, 5 and 6, the valve 52 is hollow (the portion 520 is tubular).

When the pumps 30 and 40 are at rest, the gas bubbles are discharged by lifting the valve 52. Once the bubbles have been discharged, the valve 52 returns in abutment on the body 51 in order to provide the seal between the inside of the hydraulic circuit and the liquid medium. This purge device is continuous and automatic in that it starts up as soon as a given volume of gas is present in the conduit 60.

When one of the pumps is in operation, the negative-pressure effect created by it is added to the weight of the valve 52 in order to press it against the body 51 and increase the seal on the purge device.

The watertightness of the purge device is such that, when liquid is taken off at the point 11 (circulation of the samples from the point 11 to the point 12), the suction is sufficient in the measuring chamber and, when liquid is taken off at the point 12 (circulation of the samples from the point 12 to the point 11), the quantity of liquid coming from any leakage of the purge device is small. In the latter case, the ratio between the quantity of liquid coming from the point 12 and the quantity coming from any leak from the purge device is advantageously less than the precision required for measuring the physicochemical parameters in the measuring chamber.

Preferably, the purge device 50 is placed between the measuring chamber and the takeoff point with the least depth. Thus, if the takeoff point with the least depth is close to the purge device and the latter has a leak, the liquid issuing from this leak does not falsify or only slightly falsifies the measurement since the liquid introduced into the hydraulic circuit by this leak a priori has the same physicochemical properties as the liquid taken off.

To preserve over time the watertightness of the purge device 50, the tubular body 51 and the valve 52 are advantageously produced from a material with a biocidal surface, for example made from anti-biosoiling copper alloy.

The immersion of the hydraulic circuit affords numerous advantages:
  from an energy point of view the only hydraulic work consists of circulating the liquid in the hydraulic circuit while opposing linear and singular pressure drops, which are very small because of the in-line arrangement of the elements of the hydraulic circuit; there is no work of gravity elevation of liquid to be performed;
  sealing with a liquid medium is easier to achieve than sealing in air; in addition, any microleaks at the automatic purge device do not have any consequence on the hydraulic functioning of the system;
  the immersed purge device is a very simple structure, which adds to the reliability of the measuring system;
  the system does not require a priming circuit.

Although the system of the invention preferably functions in total immersion, it can also function partly immersed. The purge device is then changed for an air-purge device, such as an airtight vacuum pump.

It should be noted that the immersed purge device illustrated in FIGS. 1 to 6 can be replaced by a more conventional device, such as a solenoid valve controlled for opening between two suction cycles of the pumps. In general terms, the purge device is placed at a high point on the hydraulic circuit on a top opening of a conduit connecting the measuring chamber to one of the pumps.

Although the invention has been described in relation to various particular embodiments, it is obvious that it is no way limited and that it comprises all the technical equivalents of the means described as well as combinations thereof if these fall within the scope of the invention.

The invention claimed is:

1. System for measuring or monitoring the quality of a liquid medium comprising first and second points for taking off a sample from the liquid medium and a hydraulic circuit in which the samples taken from said first and second sample-takeoff points circulate, said hydraulic circuit comprising:
  a measuring chamber provided with at least one measuring sensor able to measure a quantity characteristic of the liquid medium, said measuring chamber having a first opening in fluid communication with the first sample-takeoff point and a second opening,
  a first suction pump having a suction inlet connected to the second opening of the measuring chamber and a discharge opening in fluid communication with the liquid medium, the first suction pump being able, in operating configuration, to circulate in the hydraulic circuit, a sample taken from the first sample-takeoff point;
  a second suction pump having a suction inlet connected to the first opening of the measuring chamber and a discharge outlet in fluid communication with the liquid medium, said second suction pump being able, in the operating configuration, to circulate in the hydraulic circuit a sample taken from the second sample-takeoff point;

at least one conduit for connecting the first opening of the measuring chamber to the suction inlet of the second suction pump or connecting the second opening of the measuring chamber to the suction inlet of the first suction pump, said at least one conduit being provided with a purge device in order to discharge the gases present in the hydraulic circuit, and the discharge outlet of the first suction pump is connected to the second sample-takeoff point and the discharge outlet of the second suction pump is connected to the first sample-takeoff point, said first and second suction pumps being, at rest, able to allow the passage of liquid from their discharge outlet to their suction inlet.

2. System according to claim 1, wherein the first and second suction pumps are suitable for immersion and are, in the operating configuration, immersed in the liquid medium.

3. System according to claim 2, wherein the purge device is suitable for immersion and is immersed in the liquid medium.

4. System according to claim 3, wherein the purge device comprises a valve system for discharging the gases present in the hydraulic circuit.

5. System according to claim 4, wherein the purge device comprises:

a substantially vertical tubular body mounted by its bottom open end on a top opening of the conduit between the measuring chamber and the first or second suction pump, and a cylindrical valve able to slide in an internal passage in the tubular body and to cooperate with a bottom portion of the tubular body, forming a seat, in order to close off the bottom open end of said tubular body.

6. System according to claim 5, wherein an internal wall of a bottom portion of the tubular body comprises a frustoconical portion forming a seat of a valve.

7. System according to claim 6, wherein the valve comprises a bottom portion the external wall of which comprises a frustoconical portion cooperating with the frustoconical portion of the internal wall of the tubular body in order to close off the bottom open end of the tubular body.

8. System according to claim 1, wherein the hydraulic circuit comprises a means of injecting or generating a biocidal product placed between said first and second sample-takeoff points.

9. System according to claim 8, wherein said biocidal product generating means is mounted on the measuring chamber.

10. System according to claim 1, wherein said first and second suction pumps are centrifugal impeller pumps.

* * * * *